(12) United States Patent
Shinomiya et al.

(10) Patent No.: US 11,807,590 B2
(45) Date of Patent: Nov. 7, 2023

(54) METHANE PRODUCTION SYSTEM

(71) Applicant: HITACHI ZOSEN CORPORATION, Osaka (JP)

(72) Inventors: Hiroyuki Shinomiya, Osaka (JP); Hiroyuki Takano, Osaka (JP); Koichi Izumiya, Osaka (JP); Masahiro Yamaki, Osaka (JP)

(73) Assignee: Hitachi Zosen Corporation, Osaka (JP)

( * ) Notice: Subject to any disclaimer, the term of this patent is extended or adjusted under 35 U.S.C. 154(b) by 73 days.

(21) Appl. No.: 17/439,170

(22) PCT Filed: Feb. 17, 2020

(86) PCT No.: PCT/JP2020/005966
§ 371 (c)(1),
(2) Date: Sep. 14, 2021

(87) PCT Pub. No.: WO2020/189127
PCT Pub. Date: Sep. 24, 2020

(65) Prior Publication Data
US 2022/0162139 A1 May 26, 2022

(30) Foreign Application Priority Data
Mar. 19, 2019 (JP) ................. 2019-051105

(51) Int. Cl.
*C07C 1/04* (2006.01)
*C07C 1/12* (2006.01)

(52) U.S. Cl.
CPC ............... *C07C 1/041* (2013.01); *C07C 1/12* (2013.01)

(58) Field of Classification Search
CPC ... B01J 4/001; B01J 7/00; B01J 8/0278; B01J 12/007; C07C 1/041; C07C 1/12
See application file for complete search history.

(56) References Cited

U.S. PATENT DOCUMENTS

| | | | |
|---|---|---|---|
| 3,970,435 A | 7/1976 | Schultz et al. | |
| 2009/0247653 A1* | 10/2009 | Ravikumar | C10L 3/08 422/600 |
| 2014/0211274 A1 | 7/2014 | Ohta | |

FOREIGN PATENT DOCUMENTS

| | | |
|---|---|---|
| CN | 104649859 A | 5/2015 |
| DE | 102007005494 A1 | 7/2008 |

(Continued)

OTHER PUBLICATIONS

International Search Report dated May 19, 2020 issued in corresponding International Patent Application No. PCT/JP2020/005966 with English translation (4 pgs.).

*Primary Examiner* — Jafar F Parsa
(74) *Attorney, Agent, or Firm* — Pillsbury Winthrop Shaw Pittman, LLP

(57) ABSTRACT

A methane production system comprises: a reaction tank that produces methane and water by reacting CO and/or $CO_2$ supplied to the reaction tank with hydrogen; a cleaning tank that is located at an upstream side of the reaction tank in a supply direction of the CO and/or $CO_2$, and removes water-soluble impurities from a raw material gas including the CO and/or $CO_2$ and the water-soluble impurities by bringing the raw material gas into contact with water; and a first supply line that supplies the raw material gas from which the water-soluble impurities are removed from the cleaning tank to the reaction tank; and a second supply line supplies water produced in the reaction tank from the reaction tank to the cleaning tank to bring the produced water into contact with the raw material gas in the cleaning tank.

4 Claims, 2 Drawing Sheets

(56) References Cited

FOREIGN PATENT DOCUMENTS

| | | |
|---|---|---|
| JP | S51-118704 | 10/1976 |
| JP | 2005-523989 A | 8/2005 |
| JP | 2012-140382 A | 7/2012 |
| JP | 2014-148373 A | 8/2014 |
| JP | 2015-124217 A | 7/2015 |
| JP | 2016-152107 A | 8/2016 |
| JP | 2016-160309 A | 9/2016 |
| JP | 2017-052669 A | 3/2017 |
| JP | 6263029 B2 | 1/2018 |
| JP | 6299347 B2 | 3/2018 |
| WO | 03/097565 A1 | 11/2003 |

\* cited by examiner

METHANE PRODUCTION SYSTEM

CROSS-REFERENCE TO RELATED APPLICATIONS

This Application is the U.S. National Stage of PCT/JP2020/005966, filed Feb. 17, 2020, which claims priority to Japanese Patent Application No. 2019-051105, filed Mar. 19, 2019, the contents of each of which are incorporated herein by reference in their entireties.

TECHNICAL FIELD

There is a known methane production apparatus that produces methane by reacting carbon dioxide with hydrogen.

BACKGROUND ART

For example, there is a proposed methane synthesizing apparatus that includes: the first reactor vessel in which carbon monoxide and water are produced by the reaction of carbon dioxide and hydrogen; the first condenser in which the carbon monoxide and water are separated; the second reactor vessel in which the carbon monoxide is introduced from the first condenser, and methane and water are generated by the reaction of the carbon monoxide and hydrogen; and the second condenser in which the methane and water are separated (for example, see Patent Document 1).

In the methane synthesizing apparatus, carbon dioxide is reacted with hydrogen under the conditions of 460° C. to 550° C. and 3.0 MPa in the first reactor vessel as shown in the following chemical formula (1), thereby producing carbon monoxide and water.

$$CO_2 + H_2 \rightarrow CO + H_2O \tag{1}$$

Then, the gas including the carbon monoxide and water as the main components and the hydrogen as the remaining component is supplied from the first reactor vessel to the first condenser, and the water is separated and removed from the gas therein.

Subsequently, the gas from which water is separated is supplied from the first condenser to the second reactor vessel. In the second reactor vessel, the carbon monoxide is reacted with the hydrogen under the conditions of 250° C. to 450° C. and 3.0 MPa as shown in the following chemical formula (2), thereby producing methane and water.

$$CO + 3H_2 \rightarrow CH_4 + H_2O \tag{2}$$

Then, the gas including the methane and water is supplied from the second reactor vessel to the second condenser, and the water is separated and removed from the gas therein.

CITATION LIST

Patent Document

Patent Document 1: Japanese Unexamined Patent Publication No. 2012-140382

SUMMARY OF THE INVENTION

Problem to be Solved by the Invention

However, in the methane synthesizing apparatus described in Patent Document 1, the methane produced in the second reactor vessel is dissolved in the water separated by the second condenser. Methane is combustible. Thus, when the water separated by the second condenser is discharged from the methane synthesizing apparatus, concerns about the safety of the discharged water are raised. Further, the methane emitted from the water dissolving methane to the atmosphere causes the environmental burden.

The present invention provides a methane production system that can efficiently use the water produced by the reaction, improve the safety of the produced water, and reduce the environmental burden.

Means for Solving the Problem

The present invention [1] includes a methane production system comprising: a reaction tank configured to be supplied with CO and/or $CO_2$ and produce methane and water by reacting CO and/or $CO_2$ with hydrogen; a cleaning tank that is located at an upstream side of the reaction tank in a supply direction of the CO and/or $CO_2$, the cleaning tank configure to remove water-soluble impurities from a raw material gas including the CO and/or $CO_2$ and the water-soluble impurities by bringing the raw material gas into contact with water; a first supply line configured to supply the raw material gas from which the water-soluble impurities are removed from the cleaning tank to the reaction tank; and a second supply line configured to supply water produced in the reaction tank from the reaction tank to the cleaning tank to bring the produced water into contact with the raw material gas in the cleaning tank.

In the structure, the second supply line supplies the water produced in the reaction tank (hereinafter, referred to as produced water) from the reaction tank to the cleaning tank. In the cleaning tank, the raw material gas including CO and/or $CO_2$ and the water-soluble impurities can be brought into contact with the produced water.

At that time, the water-soluble impurities included in the raw material gas are dissolved into the produced water, and the methane dissolved in the produced water is replaced by CO and/or $CO_2$. Thus, the produced water can efficiently be used to remove the water-soluble impurities included in the raw material gas, and the methane dissolved in the produced water can be reduced.

As a result, the safety of the produced water can be improved, and the environmental burden can be reduced.

The present invention [2] includes the methane production system described in [1] above, wherein the reaction tank, the first supply line, the cleaning tank, and the second supply line constitute a closed path.

In the structure, the reaction tank, the first supply line, the cleaning tank, and the second supply line constitute a closed path. Thus, the discharge of methane from the methane production system can be suppressed. Thus, the environmental burden can surely be reduced.

The present invention [3] includes the methane production system described in [2] above, further comprising: a circulation line configured to circulate the water stored in the cleaning tank by connecting the cleaning tank to the second supply line; and a suction portion that is located at a connection part of the circulation line and the second supply line, the suction portion configured to suck the water from the reaction tank when negative pressure is generated in the suction portion by passage of the water from the cleaning tank.

In the structure, the circulation line circulates the produced water stored in the cleaning tank. Thus, the methane dissolved in the produced water can surely be replaced by CO and/or $CO_2$. Consequently, the safety of the produced water can surely be improved and the environmental burden can surely be reduced.

Further, the suction portion provided at the connection part of the circulation line and the second supply line generates negative pressure by the passing of the produced water circulating through the cleaning tank, and suck the produced water of the reaction tank. Thus, with a simple structure, the produced water can be circulated, and the produced water can stably be supplied from the reaction tank to the cleaning tank.

The present invention [4] includes the methane production system described in any one of the above-described [1] to [3], wherein the second supply line includes a spray nozzle that is located in the cleaning tank and configured to spray the water supplied from the reaction tank.

In the structure, the spray nozzle sprays the produced water supplied from the reaction tank into the cleaning tank. Thus, in the cleaning tank, the raw material gas including CO and/or $CO_2$ and the water-soluble impurities can efficiently be brought into contact with the produced water. As a result, the water-soluble impurities can efficiently be removed from the raw material gas, and the methane dissolved in the produced water can surely be reduced.

Effects of the Invention

The methane production system of the present invention can efficiently use the water produced by the reaction, improve the safety of the produced water, and reduce the environmental burden.

DESCRIPTION OF THE EMBODIMENTS

First Embodiment

1. Methane Production System

Figure 1:
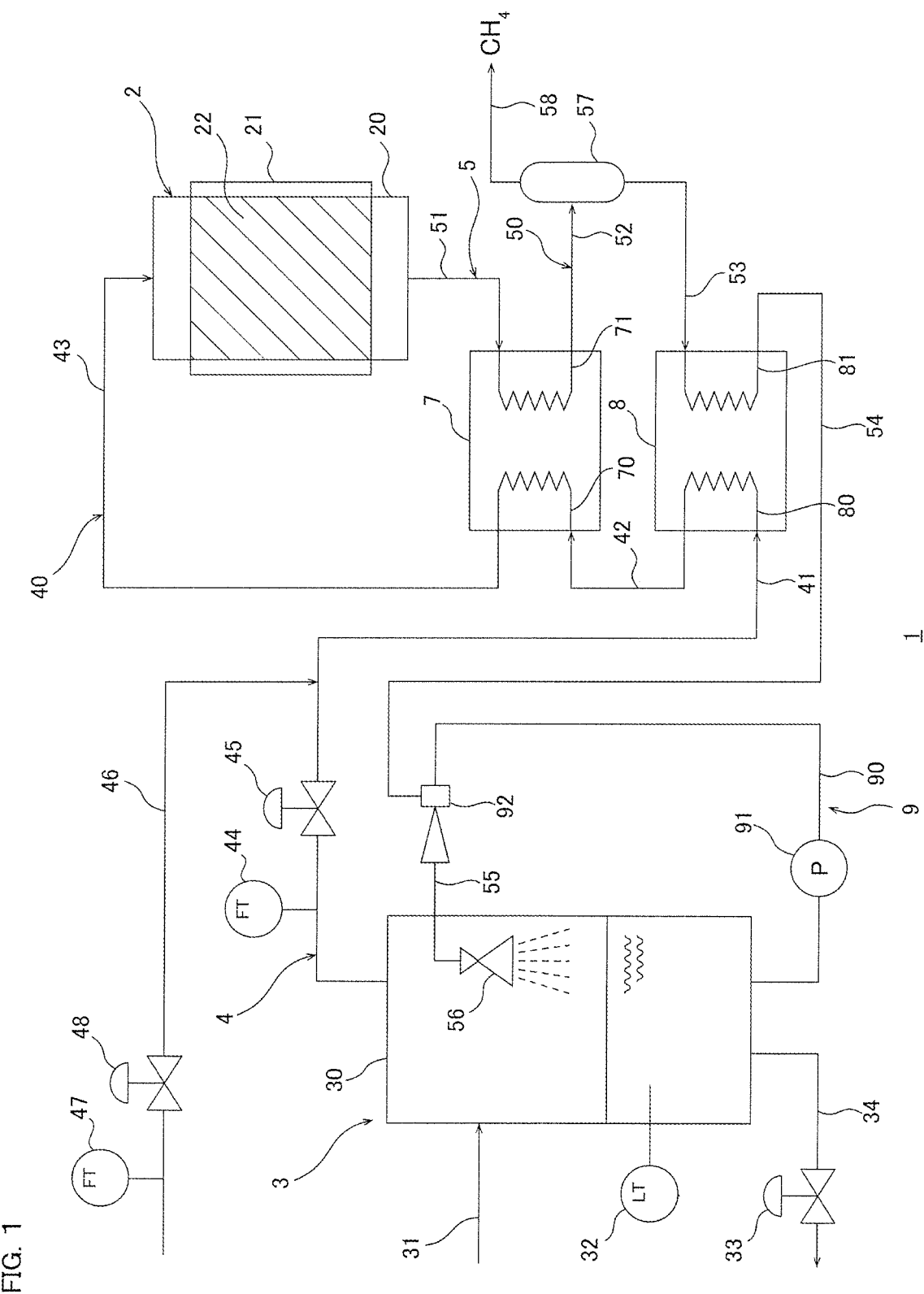
FIG. 1 is a schematic view of the first embodiment of the methane production system of the present invention.

A methane production system 1 will be described as the first embodiment of the methane production system of the present invention with reference to FIG. 1. The methane production system 1 is a methane producing facility for producing methane by reacting CO and/or $CO_2$ with hydrogen.

The methane production system 1 includes a reaction unit 2, a cleaning unit 3, a first supply unit 4, a second supply unit 5, a first heat exchanger 7, a second heat exchanger 8, and a circulation unit 9.

The reaction unit 2 that produces methane and water by reacting CO and/or $CO_2$ with hydrogen. The reaction unit 2 includes a reaction tank 20, a jacket 21, and a methanation catalyst 22.

In the reaction tank 20, CO and/or $CO_2$ are supplied, and CO and/or $CO_2$ is reacted with hydrogen, and thereby producing methane and water. Hereinafter, the water produced in the reaction tank 20 will be referred to as produced water. The reaction tank 20 is made from, for example, a heat-resistant and pressure-resistant vessel. The jacket 21 can heat the inside of the reaction tank 20.

The methanation catalyst 22 is disposed in the reaction tank 20. The methanation catalyst 22 accelerates the methanation reaction of CO and/or $CO_2$ and hydrogen. The methanation catalyst 22 includes, for example, the stabilized zirconia support, and Ni supported by the stabilized zirconia support. In the stabilized zirconia support, a stabilizing element is solid-solved. The stabilized zirconia support has a tetragonal and/or cubic crystal structure. Examples of the stabilizing element include Ca, Mn, Fe, and Co. Preferably, Mn, Fe, or Co is used. More preferably, Mn is used. Preferably, Ni is supported by the stabilized zirconia support and is solid-solved in the stabilized zirconia support.

The cleaning unit 3 washes a raw material gas including CO and/or $CO_2$ and water-soluble impurities with the produced water supplied from the reaction tank 20 to remove the water-soluble impurities from the raw material gas. The cleaning unit 3 is located at an upstream side of the reaction unit 2 in the supply direction in which CO and/or $CO_2$ are/is supplied (hereinafter, referred to as a $CO/CO_2$ supply direction). The cleaning unit 3 includes a cleaning tank 30, a raw material gas supply line 31, a water discharge line 34, an electromagnetic valve 33, and a level meter 32.

The cleaning tank 30 removes the water-soluble impurities from the raw material gas by bringing the raw material gas including the CO and/or $CO_2$ and water-soluble impurities into contact with the produced water. The cleaning tank 30 is made from, for example, a pressure-resistant vessel. The cleaning tank 30 can store the produced water after the contact with the raw material gas. The cleaning tank 30 is located at the upstream side of the reaction tank 20 in the $CO/CO_2$ supply direction.

The raw material gas supply line 31 is the piping for supplying the raw material gas to the cleaning tank 30. Although not illustrated, an upstream end of the raw material gas supply line 31 in the $CO/CO_2$ supply direction is connected to the raw material gas storage tank storing the raw material gas. A downstream end of the raw material gas supply line 31 in the $CO/CO_2$ supply direction is connected to a side wall of the cleaning tank 30.

The water discharge line 34 is the piping for discharging the produced water stored in the cleaning tank 30 from the cleaning tank 30. An upstream end of the water discharge line 34 in a discharge direction in which the produced water is discharged is connected to a bottom wall of the cleaning tank 30. Although not illustrated, a downstream end of the water discharge line 34 in the discharge direction of the produced water is connected to a discharged water storage tank storing the produced water discharged from the water discharge line 34.

The electromagnetic valve 33 is provided on the water discharge line 34. The electromagnetic valve 33 is, for example, a known on/off valve and opens and closes the water discharge line 34. The electromagnetic valve 33 usually closes the water discharge line 34. The electromagnetic valve 33 is electrically connected to a controller not illustrated.

The level meter 32 can detect the water level in the cleaning tank 30. The level meter 32 is electrically connected to the controller not illustrated. The controller not illustrated makes the electromagnetic valve 33 open the water discharge line 34 to discharge the produced water from the cleaning tank 30 when the level meter 32 detects that the water level in the cleaning tank 30 becomes a first predetermined value or more. Thereafter, the controller not illustrated makes the electromagnetic valve 33 close the water discharge line 34 to stop the discharge of the produced water from the cleaning tank 30 when the level meter 32 detects that the water level in the cleaning tank 30 becomes a second predetermined value or less, or less than the first predetermined value.

The first supply unit 4 mixes the raw material gas, from which the water-soluble impurities are removed by the washing in the cleaning tank 30 (hereinafter, referred to as a washed raw material gas), with a hydrogen gas, and then supplies the mixed gas thereof to the reaction tank 20. The first supply unit 4 includes a first supply line 40, a hydrogen supply line 46, a first electromagnetic valve 45, a first flowmeter 44, a second electromagnetic valve 48, and a second flowmeter 47.

The first supply line 40 supplies the washed raw material gas from the cleaning tank 30 to the reaction tank 20. The first supply line 40 is located between the cleaning tank 30 and the reaction tank 20 in the $CO/CO_2$ supply direction. The first supply line 40 includes a first part 41, a second heating-side flow path 80 constituting the second heat exchanger 8 described below, a second part 42, a first heating-side flow path 70 constituting the first heat exchanger 7 described below, and a third part 43 in order in the $CO/CO_2$ supply direction. The first heating-side flow path 70 and second heating-side flow path 80 will be described below.

The first part 41 is the piping for supplying the washed raw material gas from the cleaning tank 30 to the second heat exchanger 8. An upstream end of the first part 41 in the $CO/CO_2$ supply direction is connected to an upper wall of the cleaning tank 30. A downstream end of the first part 41 in the $CO/CO_2$ supply direction is connected to an upstream end of the second heating-side flow path 80 in the $CO/CO_2$ supply direction.

The hydrogen supply line 46 described below is connected to the first part 41. Thus, in the first part 41, the washed raw material gas and the hydrogen gas are mixed, and the mixed gas thereof is supplied to the second heating-side flow path 80.

The second part 42 is the piping for supplying the mixed gas from the second heat exchanger 8 to the first heat exchanger 7 after the mixed gas passes through the second heating-side flow path 80. An upstream end of the second part 42 in the $CO/CO_2$ supply direction is connected to a downstream end of the second heating-side flow path 80 described below in the $CO/CO_2$ supply direction. A downstream end of the second part 42 in the $CO/CO_2$ supply direction is connected to an upstream end of the first heating-side flow path 70 described below in the $CO/CO_2$ supply direction.

The third part 43 is the piping for supplying the mixed gas from the first heat exchanger 7 to the reaction tank 20 after the mixed gas passes through the first heating-side flow path 70. An upstream end of the third part 43 in the $CO/CO_2$ supply direction is connected to a downstream end of the first heating-side flow path 70 described below in the $CO/CO_2$ supply direction. A downstream end of the third part 43 in the $CO/CO_2$ supply direction is connected to an upper wall of the reaction tank 20 in the $CO/CO_2$ supply direction.

The hydrogen supply line 46 is the piping for supplying the hydrogen gas to the first supply line 40. Although not illustrated, an upstream end of the hydrogen supply line 46 in the hydrogen gas supply direction is connected to a hydrogen gas storage tank storing the hydrogen gas. A downstream end of the hydrogen supply line 46 in the hydrogen gas supply direction is connected to the first part 41.

The first electromagnetic valve 45 is provided on the first part 41 of the first supply line 40. The first electromagnetic valve 45 is located at an upstream side relative to a connection part of the hydrogen supply line 46 of the first part 41 in the $CO/CO_2$ supply direction. The first electromagnetic valve 45 is, for example, a known on/off valve and opens and closes the first part 41. The first electromagnetic valve 45 is electrically connected to the controller not illustrated.

The first flowmeter 44 can detect the volume of flow of the washed raw material gas passing through the first part 41. The first flow meter 44 is provided between the cleaning tank 30 and the first electromagnetic valve 45 in the first part 41. The first flow meter 44 is electrically connected to the controller not illustrated. The controller not illustrated appropriately opens or closes the first electromagnetic valve 45 so that the volume of flow of the raw material gas detected by the first flow meter 44 is a predetermined volume.

The second electromagnetic valve 48 is provided on the hydrogen supply line 46. The second electromagnetic valve 48 is, for example, a known on/off valve, and opens and closes the hydrogen supply line 46. The second electromagnetic valve 48 is electrically connected to the controller not illustrated.

The second flow meter 47 can detect the volume of flow of the hydrogen gas passing through the hydrogen supply line 46. The second flow meter 47 is provided at an upstream side relative to the second electromagnetic valve 48 in the hydrogen gas supply direction on the hydrogen supply line 46. The second flow meter 47 is electrically connected to the controller not illustrated. The controller not illustrated appropriately opens or closes the second electromagnetic valve 48 so that the volume of flow of the hydrogen gas detected by the second flow meter 47 is a predetermined volume.

The second supply unit 5 separates the reaction product produced in the reaction tank 20 into the produced water and methane and supplies the produced water to the cleaning tank 30 and the methane to a methane storage tank not illustrated. The second supply unit 5 includes a gas-liquid separator 57, a second supply line 50, and a methane discharge line 58.

The gas-liquid separator 57 is located at a downstream side of the reaction tank 20 in the supply direction in which the produced water is supplied. The gas-liquid separator 57 can separate the reaction product supplied from the reaction tank 20 into the produced water and methane.

The second supply line 50 supplies the produced water from the reaction tank 20 to the cleaning tank 30 so as to bring the produced water into contact with the raw material gas in the cleaning tank 30. The second supply line 50 includes a first part 51, a first cooling-side flow path 71 constituting the first heat exchanger 7 described below, a second part 52, a third part 53, a second cooling-side flow path 81 constituting the second heat exchanger 8, a fourth part 54, a fifth part 55, and a spray nozzle 56 in order in the supply direction of the produced water. The first cooling-side flow path 71 and second cooling-side flow path 81 will be described below.

The first part 51 is the piping for supplying the reaction product from the reaction tank 20 to the first heat exchanger 7. An upstream end of the first part 51 in the supply direction of the produced water is connected to a bottom wall of the reaction tank 20. A downstream end of the first part 51 in the supply direction of the produced water is connected to an upstream end of the first cooling-side flow path 71 described below in the supply direction of the produced water.

The second part 52 is the piping for supplying the reaction product from the first heat exchanger 7 to the gas-liquid separator 57 after the reaction product passes through the first cooling-side flow path 71. An upstream end of the second part 52 in the supply direction of the produced water is connected to a downstream end of the first cooling-side flow path 71 described below in the supply direction of the produced water. A downstream end of the second part 52 in the supply direction of the produced water is connected to the gas-liquid separator 57.

The third part 53 is the piping for supplying the produced water separated in the gas-liquid separator 57 from the gas-liquid separator 57 to the second heat exchanger 8 described below. An upstream end of the third part 53 in the supply direction of the produced water is connected to the gas-liquid separator 57. A downstream end of the third part 53 in the supply direction of the produced water is connected to an upstream end of the second cooling-side flow path 81 described below in the supply direction of the produced water.

The fourth part 54 is the piping for supplying the produced water from the second heat exchanger 8 to an ejector 92 described below after the produced water passes through the second cooling-side flow path 81. An upstream end of the fourth part 54 in the supply direction of the produced water is connected to a downstream end of the second cooling-side flow path 81 in the supply direction of the produced water. A downstream end of the fourth part 54 in the supply direction of the produced water is connected to a first entrance (not illustrated) of the ejector 92.

The fifth part 55 is the piping for supplying the produced water to the cleaning tank 30 after the produced water passes through the ejector 92. An upstream end of the fifth part 55 in the supply direction of the produced water is connected to an exit of the ejector 92 (not illustrated). A downstream end of the fifth part 55 in the supply direction of the produced water is located in the cleaning tank 30.

The spray nozzle 56 is provided at a downstream end of the second supply line 50 in the supply direction of the produced water, namely, a downstream end of the fifth part 55 in the supply direction of the produced water. The spray nozzle 56 is located in the cleaning tank 30. The spray nozzle 56 sprays the produced water supplied from the reaction tank 20.

In this manner, the cleaning tank 30, the first supply line 40, the reaction tank 20, the second supply line 50, and the gas-liquid separator 57 constitute a closed path.

The methane discharge line 58 is the piping for discharging the methane gas separated in the gas-liquid separator 57 from the gas-liquid separator 57. An upstream end of the methane discharge line 58 in a methane discharge direction is connected to the gas-liquid separator 57. Although not illustrated, a downstream end of the methane discharge line 58 in the methane discharge direction is connected to the methane storage tank storing the methane discharged from the methane discharge line 58.

The first heat exchanger 7 transfers heat between the reaction product supplied from the reaction tank 20 and the mixed gas of the washed raw material gas and the hydrogen gas. The first heat exchanger 7 includes the above-described first heating-side flow path 70 and the above-described first cooling-side flow path 71. In the first heating-side flow path 70, the mixed gas having a relatively low temperature passes. In the first cooling-side flow path 71, the reaction product having a relatively high temperature passes. Thus, in the first heat exchanger 7, the heat moves from the reaction product passing through the first cooling-side flow path 71 to the mixed gas passing through the first heating-side flow path 70.

The second heat exchanger 8 transfers heat between the produced water separated in the gas-liquid separator 57 and the mixed gas of the washed raw material gas and the hydrogen gas. The second heat exchanger 8 includes the above-described second heating-side flow path 80 and the above-described second cooling-side flow path 81. In the second heating-side flow path 80 the mixed gas having a relatively low temperature passes. In the second cooling-side flow path 81, the produced water having a relatively high temperature passes. Thus, in the second heat exchanger 8, the heat moves from the produced water passing through the second cooling-side flow path 81 to the mixed gas passing through the second heating-side flow path 80.

The circulation unit 9 circulates the produced water stored in the cleaning tank 30. The circulation unit 9 includes a circulation line 90, a pump 91, and an ejector 92 as an example of a suction portion.

The circulation line 90 circulates the produced water store in the cleaning tank 30. The circulation line 90 connects the cleaning tank 30 to the second supply line 50. In detail, an upstream end of the circulation line 90 in a circulation direction in which the produced water circulates is connected to a bottom wall of the cleaning tank 30. A downstream end of the circulation line 90 in the produced water circulation direction is connected to a second entrance (not illustrated) of the ejector 92.

The pump 91 is provided on the circulation line 90. The pump 91 is, for example, a known liquid transfer pump.

The ejector 92 is provided at a connection part of the circulation line 90 and the second supply line 50. In details, the ejector 92 is provided at a connection part of the fourth part 54, the fifth part 55, and the circulation line 90. Negative pressure is generated inside the ejector 92 when the pump 91 activates and allows the produced water from the cleaning tank 30 to pass through the ejector 92 from the circulation line 90 toward the fifth part 55. In this manner, the produced water supplied from the fourth part 54 is sucked in the ejector 92. In other words, the passage of the produced water from the cleaning tank 30 generates negative pressure in the ejector 92, and the ejector 92 sucks the produced water from the reaction tank 20.

2. Method of Producing Methane

Next, a method of producing methane in the methane production system 1 of the first embodiment will be described.

In the method of producing methane, a raw material gas is supplied from the raw material gas supply line 31 to the cleaning tank 30. The raw material gas is produced, for example, in a thermal power plant, a waste incineration plant, a sewage treatment plant, a methane fermentation facility, or natural gas mining. The raw material gas includes CO and/or $CO_2$, and water-soluble impurities. In the embodiment, a case in which a raw material gas includes $CO_2$ and water-soluble impurities will be described in detail. Examples of the water-soluble impurities include hydrogen sulfide, ammonia, and hydrogen chloride. These water-soluble impurities poison the methanation catalyst 22 and thus should be removed as much as possible.

The raw material gas to be supplied to the cleaning tank 30 has a temperature of, for example, 0° C. or more, preferably 5° C. or more and, for example, 35° C. or less, preferably 20° C. or less.

Then, the raw material gas comes into contact with the produced water (methane-dissolved water described below)

supplied from the reaction tank 20 in the cleaning tank 30. In this manner, the water-soluble impurities in the raw material gas are dissolved into the produced water and removed from the raw material gas. At that time, the methane dissolved in the produced water is replaced by $CO_2$. The replacement of methane by $CO_2$ will be described in detail below.

The pressure (gauge pressure) in the cleaning tank 30 is, for example, 0.1 MPaG or more, preferably 0.6 MPaG or more and, for example, 1 MPaG or less, preferably 0.9 MPaG or less.

Subsequently, the raw material gas (the washed raw material gas) from which the water-soluble impurities are removed flows from the cleaning tank 30 into the first part 41 of the first supply line 40. Then, the washed raw material gas is mixed with the hydrogen gas supplied from the hydrogen supply line 46 in the first part 41 so that the molar ratio of $CO_2$ to hydrogen is 1:4. The volume of flow of the washed raw material gas is adjusted by the first flow meter 44 and the first electromagnetic valve 45. The volume of flow of the hydrogen gas is adjusted by the second flow meter 47 and the second electromagnetic valve 48.

Subsequently, the mixed gas of the washed raw material gas and the hydrogen gas is supplied to the second heating-side flow path 80. When passing through the second heating-side flow path 80, the mixed gas is heated by the produced water passing through the second cooling-side flow path 81.

After passing through the second heating-side flow path 80, the mixed gas has a temperature of, for example, 10° C. or more, preferably 40° C. or more and, for example, 200° C. or less, more preferably 100° C. or less.

Subsequently, after passing through the second heating-side flow path 80, the mixed gas is supplied through the second part 42 to the first heating-side flow path 70. When passing through the first heating-side flow path 70, the mixed gas is heated by the reaction product passing through the first cooling-side flow path 71.

After passing through the first heating-side flow path 70, the mixed gas has a temperature of, for example, 100° C. or more, preferably 150° C. or more, more preferably 200° C. or more and, for example, 300° C. or less, preferably 250° C. or less.

Subsequently, after passing through the first heating-side flow path 70, the mixed gas is supplied through the third part 43 to the reaction tank 20.

Consequently, in the reaction tank 20, as shown in the following chemical equation (1), by the reaction of $CO_2$ and hydrogen, methane and water (the produced water) are produced.

[Chemical Formula 1]

$$4H_2 + CO_2 \rightleftharpoons CH_4 + 2H_2O \quad (1)$$

The temperature inside the reaction tank 20 is, for example, 200° C. or more, preferably 250° C. or more and, for example, 700° C. or less, preferably 650° C. or less.

The pressure (gauge pressure) inside the reaction tank 20 is, for example, 0 MPaG or more, preferably 0.4 MPaG or more and, for example, 1 MPaG or less, preferably 0.9 MPaG or less.

The partial pressure (gauge pressure) of methane in the reaction tank 20 is, for example, 0.1 MPaG or more, preferably 0.3 MPaG or more and, for example, 0.9 MPaG or less, preferably 0.5 MPaG or less.

The partial pressure (gauge pressure) of $CO_2$ in the reaction tank 20 is, for example, 0.001 MPaG or more, preferably 0.003 MPaG or more and, for example, 0.009 MPaG or less, preferably 0.005 MPaG or less.

The partial pressure (gauge pressure) of hydrogen in the reaction tank 20 is, for example, 0.004 MPaG or more, preferably 0.012 MPaG or more and, for example, 0.036 MPaG or less, preferably 0.02 MPaG or less.

Subsequently, the reaction product including the methane and the produced water is discharged from the reaction tank 20 through the first part 51 of the second supply line 50.

The reaction product has a temperature of, for example, 150° C. or more, preferably 200° C. or more and, for example, 350° C. or less, preferably 250° C. or less.

Subsequently, the reaction product is supplied through the first part 51 to the first cooling-side flow path 71. Then, when passing through the first cooling-side flow path 71, the reaction product is cooled down by the mixed gas passing through the first heating-side flow path 70.

After passing through the first cooling-side flow path 71, the reaction product has a temperature of, for example, 5° C. or more, preferably 20° C. or more and, for example, 110° C. or less, preferably less than 100° C.

Where, after passing through the first cooling-side flow path 71, the reaction product has a temperature of the upper limit or less, the water can be kept at the boiling point or less under the internal pressure of the second supply line 50. Thus, a sufficient amount of water to be supplied to the cleaning tank 30 can surely be saved to remove the water-soluble impurities in the raw material gas.

Subsequently, after passing through the first cooling-side flow path 71, the reaction product is supplied through the second part 52 to the gas-liquid separator 57.

Then, the gas-liquid separator 57 separates the reaction product into produced water and methane.

At that time, the gas-liquid separator 57 has a temperature of, for example, 5° C. or more, preferably 20° C. or more and, for example, 110° C. or less, preferably less than 100° C.

Thereafter, the methane is stored through the methane discharge line 58 in the methane storage tank not illustrated. Alternatively, an apparatus (such as a heat exchanger or a gas-liquid separator) that traps the condensed water may be provided between the gas-liquid separator 57 and the methane storage tank not illustrated on the methane discharge line 58.

Further, the produced water is supplied through the third part 53 to the second cooling-side flow path 81. Here, methane is dissolved in the produced water separated in the gas-liquid separator 57. Hereinafter, the produced water dissolving methane is referred to as methane-dissolved water.

The amount of the methane dissolved in the methane-dissolved water relative to the total mass of the methane-dissolved water is, for example, 50 ppm or more, preferably 100 ppm or more and, for example, 150 ppm or less, preferably 130 ppm or less. The amount of the dissolved methane can be measured by a detector (the same will apply hereinafter).

Thereafter, when passing through the second cooling-side flow path 81, the methane-dissolved water is cooled down by the mixed gas passing through the second heating-side flow path 80.

After passing through the second cooling-side flow path 81, the methane-dissolved water has a temperature of, for example, 5° C. or more, preferably 20° C. or more and, for example, 100° C. or less, preferably 60° C. or less.

Subsequently, after passing through the second cooling-side flow path 81, the methane-dissolved water is supplied through the fourth part 54 and fifth part 55 to the spray nozzle 56.

Then, the methane-dissolved water is sprayed from the spray nozzle 56 and comes into contact with the raw material gas supplied from the raw material gas supply line 31.

Methane is less soluble than $CO_2$ in water. In the cleaning tank 30, $CO_2$ exists in large excess over the methane. Thus, the methane dissolved in the produced water is replaced by $CO_2$ in the cleaning tank 30. At that time, as described above, the water-soluble impurities in the raw material gas are dissolved into the produced water. In other words, the water-soluble impurities and $CO_2$ are dissolved into the produced water while the methane is discharged from the produced water.

Thereafter, the methane discharged from the produced water flows together with the washed raw material gas into the first part 41 of the first supply line 40 from the cleaning tank 30.

The produced water dissolving the water-soluble impurities and $CO_2$ is stored in the cleaning tank 30 and transferred through the circulation line 90 to the ejector 92 by the pump 91. When the produced water is passing through the ejector 92 from the circulation line 90 toward the fifth part 55, negative pressure is generated inside the ejector 92 and the ejector 92 sucks the methane-dissolved water from the fourth part 54. In this manner, the produced water from the circulation line 90 and the methane-dissolved water from the fourth part 54 converge and are sprayed from the spray nozzle 56.

Thereafter, when the level meter 32 detects that the water level in the cleaning tank 30 is the first predetermined value or more, the controller not illustrated makes the electromagnetic valve 33 open the water discharge line 34 to discharge the produced water from the cleaning tank 30.

The amount of the $CO_2$ dissolved in the produced water discharged from the water discharge line 34 relative to the total mass of the discharged produced water is, for example, 1000 ppm or more, preferably 2000 ppm or more, more preferably 5000 ppm or more. The amount of the dissolved $CO_2$ can be measured by a detector.

3. Operations and Effects

As illustrated in FIG. 1, the second supply line 50 supplies the produced water produced in the reaction tank 20 from the reaction tank 20 to the cleaning tank 30. In the cleaning tank 30, the raw material gas including the CO and/or $CO_2$ and water-soluble impurities is brought into contact with the produced water.

At that time, the water-soluble impurities included in the raw material gas are dissolved into the produced water, and the methane dissolved in the produced water is replaced by the $CO_2$. Thus, the produced water can efficiently be used to remove the water-soluble impurities included in the raw material gas, and the methane dissolved in the produced water can be reduced. As a result, the safety of the produced water can be improved, and the environmental burden can be reduced.

Further, the cleaning tank 30, the first supply line 40, the reaction tank 20, the second supply line 50, and the gas-liquid separator 57 constitute a closed path. Thus, the discharge of methane from the methane production system 1 can be suppressed. As a result, the environmental burden can surely be reduced.

Furthermore, the circulation line 90 circulates the produced water stored in the cleaning tank 30. Thus, the methane dissolved in the produced water can surely be replaced by the $CO_2$. As a result, the safety of the produced water can be improved, and the environmental burden can more surely be reduced.

However, in the methane production system 1, the cleaning tank 30 to which the raw material gas is supplied has the highest internal pressure. In the order from the first supply line 40, the reaction tank 20, to the second supply line 50, the internal pressures thereof become smaller. Thus, to supply the produced water from the reaction tank 20 to the cleaning tank 30 in order to remove the water-soluble impurities in the raw material gas by the produced water, a mechanism for feeding the produced water using pressure is required.

In light of the foregoing, in the methane production system 1, the ejector 92 is provided at the connection part of the circulation line 90 and the second supply line 50. The passage of the produced water circulating through the cleaning tank 30 generates negative pressure in the ejector 92, and the ejector 92 sucks the produced water from the reaction tank 20. Thus, with a simple structure, the produced water can be circulated, and the produced water can stably be supplied from the reaction tank 20 to the cleaning tank 30.

Further, the spray nozzle 56 sprays the produced water supplied from the reaction tank 20 into the cleaning tank 30. Thus, in the cleaning tank 30, the raw material gas including the $CO_2$ and water-soluble impurities can efficiently be brought into contact with the produced water. As a result, the water-soluble impurities can efficiently be removed from the raw material gas, and the methane dissolved in the produced water can surely be reduced.

Furthermore, by the pump 91 and the spray nozzle 56, the number of times of the contact of the produced water with the raw material gas can be increased. Thus, the number of times of the absorption of the water-soluble impurities into the produced water can be increased.

In the above-described first embodiment, the raw material gas includes the $CO_2$ and water-soluble impurities. However, the composition of the raw material gas is not limited to that of the first embodiment. The raw material gas may include CO and water-soluble impurities, or $CO_2$, CO, and water-soluble impurities. These compositions can have the same operations and effects as those of the above-described first embodiment.

4. Second Embodiment

Next, with reference to FIG. 2, the second embodiment of the present invention will be described.

In the first embodiment, as illustrated in FIG. 1, the methane production system 1 includes the two heat exchangers. However, the structure of the methane production system 1 is not limited to that.

Figure 2:
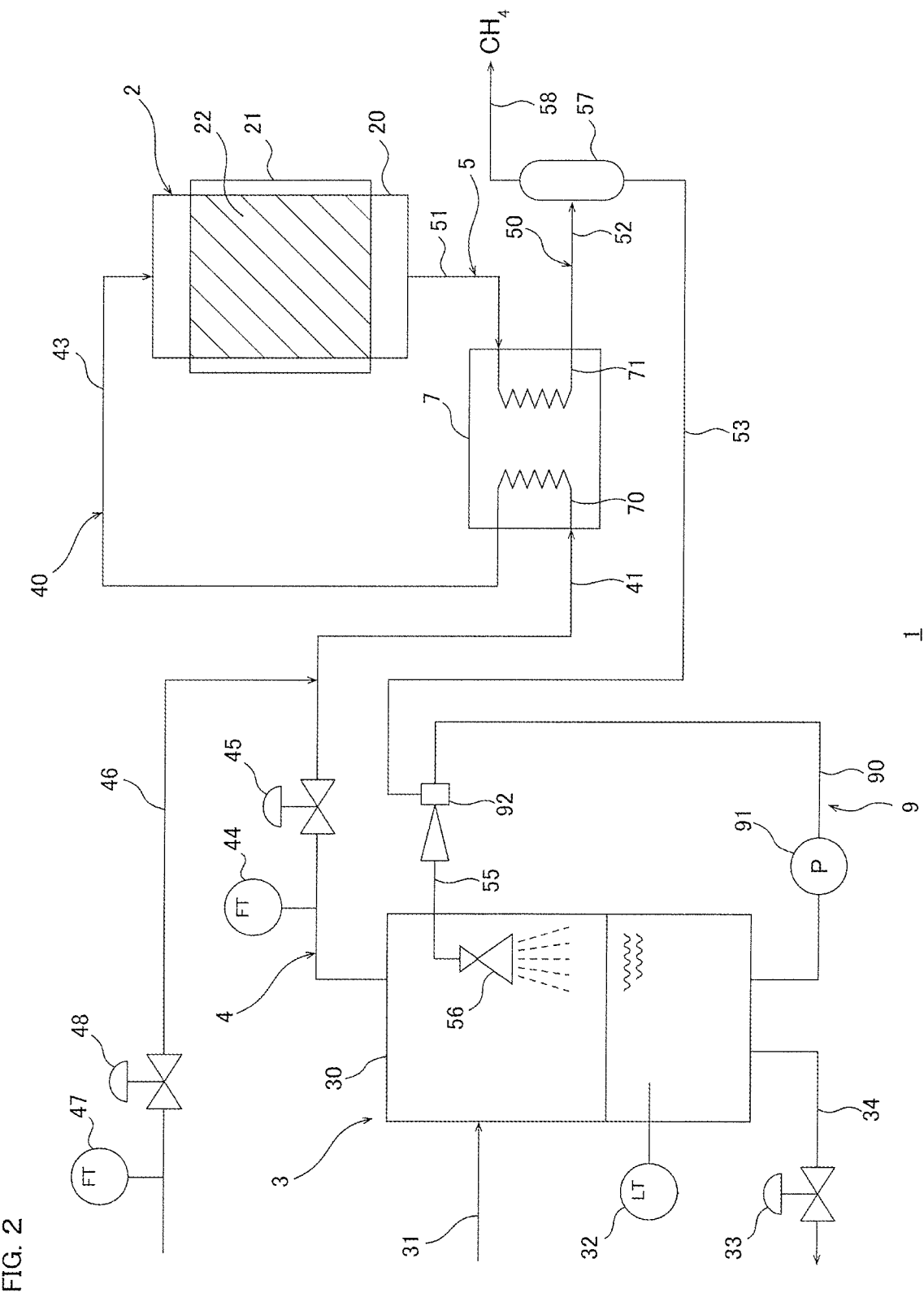
FIG. 2 is a schematic view of the second embodiment of the methane production system of the present invention.

In the second embodiment, as illustrated in FIG. 2, a methane production system 1 does not include a second heat exchanger 8 and includes only a first heat exchanger 7. Specifically, a downstream end of a first part 41 in a $CO/CO_2$ supply direction in the first supply line 40 is connected to an upstream end of a first cooling-side flow path 71. Meanwhile, a downstream end of a second part 52 in a supply direction of the produced water in the second supply line 50 is connected to a gas-liquid separator 57. At the same time, a downstream end in the supply direction of the produced water of a third part 53 in the second supply line 50 is connected to an ejector 92.

The second embodiment can have the same operations and effects as those of the above-described first embodiment.

5. Variation

In the first embodiment, the methane production system 1 includes the two heat exchangers. In the second embodiment, the methane production system 1 includes the single heat exchanger. However, the present invention is not limited to them. The number of the heat exchangers is appropriately changed depending on the conditions. Alternatively, the methane production system 1 can include no heat exchanger. However, for the heat utilization in the methane production system 1, similarly to the first embodiment and the second embodiment, the methane production system 1 preferably includes the heat exchanger(s).

In the first embodiment and the second embodiment, the hydrogen supply line 46 is connected to the first part 41 of the first supply line 40. However, the connection part of the hydrogen supply line 46 is not especially limited. For example, the hydrogen supply line 46 may be connected to any one of the parts (the first part 41 to the third part 43) of the first supply line 40. Alternatively, the hydrogen supply line 46 can directly be connected to the reaction tank 20 to separately supply the hydrogen gas and the washed raw material gas to the reaction tank 20.

However, because the hydrogen gas supplied from the hydrogen supply line 46 can be heated together with the washed raw material gas supplied from the first supply line 40, similarly to the first embodiment and the second embodiment, the hydrogen supply line 46 is preferably connected to the first supply line 40 at an upstream side relative to the heat exchanger in the CO/CO$_2$ supply direction.

Alternatively, the methane gas produced in the reaction tank 20 can directly be collected from the reaction tank 20. However, for the heat utilization in the methane production system 1, similarly to the first embodiment and the second embodiment, preferably after the reaction product produced in the reaction tank 20 passes through the heat exchanger, the gas-liquid separator separates methane and the produced water. Especially, for thermal efficiency, similarly to the first embodiment, the gas-liquid separator is preferably provided between the first heat exchanger 7 and the second heat exchanger 8 to separate methane and the produced water.

In the first embodiment and the second embodiment, the produced water is sucked by the ejector 92 and supplied to the cleaning tank 30. However, the present invention is not limited to it. By providing a pump on the second supply line 50, the produced water can be fed to the cleaning tank 30 using the pressure.

Alternatively, the methane production system 1 may include a gas detector capable of detecting the methane gas. The methane production system 1 including the gas detector can detect the leakage of the methane gas and abnormal conditions such as damage to the device (for example, the heat exchanger).

The above-described variations can also have the same operations and effects as those of the above-described first embodiment.

While the illustrative embodiments of the present invention are provided in the above description, such is for illustrative purpose only and it is not to be construed as limiting in any manner. Modification and variation of the present invention that will be obvious to those skilled in the art is to be covered by the following claims.

INDUSTRIAL APPLICABILITY

The methane production system of the present invention is preferably used to produce methane from CO and/or CO$_2$.

DESCRIPTION OF REFERENCE NUMERALS 1 methane production system
20 reaction tank
30 cleaning tank
40 first supply line
50 second supply line
56 spray nozzle
90 circulation line
92 ejector

The invention claimed is:

1. A methane production system comprising:
a reaction tank configured to be supplied with CO and/or CO$_2$ and produce methane and water by reacting CO and/or CO$_2$ with hydrogen;
a cleaning tank that is located at an upstream side of the reaction tank in a supply direction of the CO and/or CO$_2$, the cleaning tank configure to remove water-soluble impurities from a raw material gas including the CO and/or CO$_2$ and the water-soluble impurities by bringing the raw material gas into contact with water;
a first supply line configured to supply the raw material gas from which the water-soluble impurities are removed from the cleaning tank to the reaction tank; and
a second supply line configured to supply water produced in the reaction tank from the reaction tank to the cleaning tank to bring the produced water into contact with the raw material gas in the cleaning tank.

2. The methane production system according to claim 1, wherein
the reaction tank, the first supply line, the cleaning tank, and the second supply line constitute a closed path.

3. The methane production system according to claim 2, further comprising:
a circulation line configured to circulate the water stored in the cleaning tank by connecting the cleaning tank to the second supply line; and
a suction portion that is located at a connection part of the circulation line and the second supply line, the suction portion configured to suck the water from the reaction tank when negative pressure is generated in the suction portion by passage of the water from the cleaning tank.

4. The methane production system according to claim 1, wherein the second supply line includes a spray nozzle that is located in the cleaning tank and configured to spray the water supplied from the reaction tank.

* * * * *